United States Patent [19]

Ramos

[11] 4,380,090
[45] Apr. 19, 1983

[54] HIP PROSTHESIS

[76] Inventor: Pedro A. Ramos, 1960 SW. 27th Ave., Miami, Fla.

[21] Appl. No.: 356,881

[22] Filed: Mar. 10, 1982

Related U.S. Application Data

[63] Continuation-in-part of Ser. No. 286,532, Jul. 24, 1981, abandoned, which is a continuation-in-part of Ser. No. 177,791, Aug. 13, 1980, abandoned.

[51] Int. Cl.³ .......................... A61F 1/24; A61F 1/00
[52] U.S. Cl. .................................. 3/1.912; 3/1.913; 128/92 C
[58] Field of Search .................. 3/1.9–1.913; 128/92 C, 92 CA

[56] References Cited

U.S. PATENT DOCUMENTS

| 3,698,017 | 10/1972 | Scales et al. | 3/1.912 |
| 3,848,272 | 11/1974 | Noiles | 128/92 C X |
| 3,863,273 | 2/1975 | Averill | 3/1.913 X |
| 3,875,593 | 4/1975 | Shersher | 3/1.912 |
| 3,916,451 | 11/1975 | Buechel et al. | 3/1.912 X |
| 4,044,403 | 8/1977 | D'Errico | 3/1.913 |
| 4,135,517 | 1/1979 | Reale | 3/1.913 X |
| 4,172,296 | 10/1979 | D'Errico | 3/1.912 |

Primary Examiner—Ronald L. Frinks
Attorney, Agent, or Firm—Erwin M. Barnett

[57] ABSTRACT

An artificial hip joint including an artificial hip socket having a first cavity and an inner groove, a bearing insert registerable with said first cavity and itself having a second cavity and an annular bearing which has a circumferential front notch. The bearings abut the inner walls of said first cavity to define a central cavity. A locking ring is registerable with said notch and groove. An artificial femur component has a ball registerable and lockable in said central cavity.

6 Claims, 7 Drawing Figures

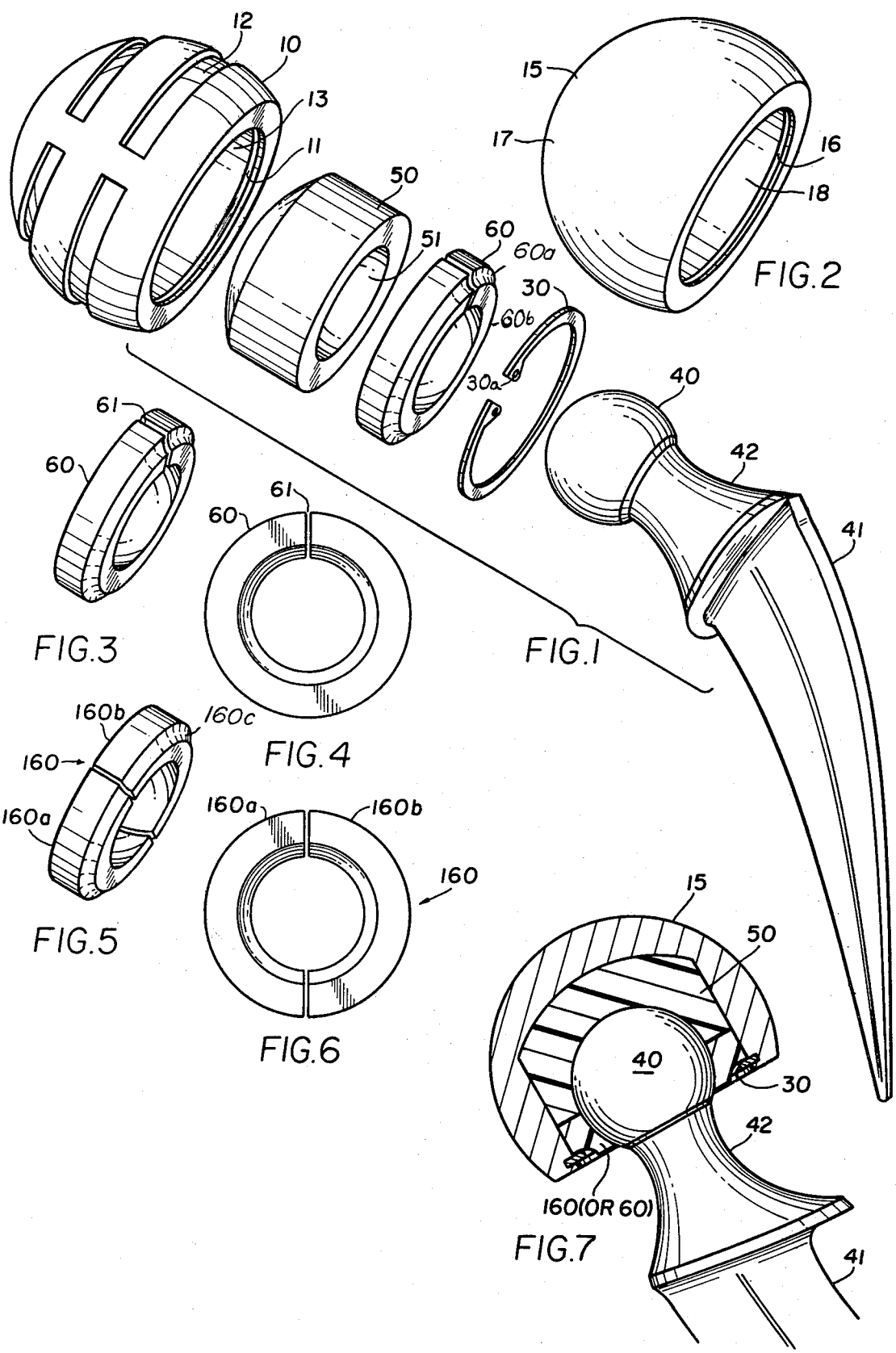

HIP PROSTHESIS

BACKGROUND OF INVENTION

This application is a continuation-in-part of co-pending patent application Ser. No. 286,532 filed July 24, 1981 and which is a continuation-in-part of co-pending patent application Ser. No. 177,791, filed Aug. 13, 1980, both now abandoned and both said applications being incorporated herein by reference.

This invention relates to artificial hip joints. In particular it relates to artificial hip joints which can be used both as a total joint, that is totally adhered to the biological surface, or a polycentric joint which is not totally adhered. A polycentric joint is used in younger people, while a total artificial hip joint is used in older people who have bad cases of arthritis. The general procedure for using an artificial hip joint is to remove the diseased or arthritic tissue and install a socket in the hip. Where the socket is movable it is polycentric, where it is not movable it is referred to as being totally adhered to the hip. After a total hip joint is installed the femur bone of the leg is cut so as to remove the head of the femur surgically. In both the polycentric and total hip joints an artificial head is provided which has a ball which fits into the socket.

Various artificial hip joints have been described in the prior art. Giliberty, U.S. Pat. No. 3,813,699 describes an artificial hip joint which includes a low friction liner between the socket and the artificial femur ball or head. Averill, U.S. Pat. No. 3,863,273 describes a bearing insert for engaging the ball of the femur. D'Errico, U.S. Pat. No. 4,044,403 also describes an insert between the socket and the ball as does Reale, U.S. Pat. No. 4,135,517 and D'Errico, U.S. Pat. No. 4,172,296. However, none of the prior art that I have seen with the exception of my co-pending applications, gives an opportunity to the surgeon to first prepare a polycentric artificial hip joint and then at any time convert it where required to a total or completely adhered hip joint, wherein a locking mechanism maintains all the components as a unit.

One object of the present invention is to provide a novel artificial hip joint which gives greater flexibility to the surgeon.

Other objects and advantages of this invention will be apparent from the description and claims which follow taken together with the appended drawings.

SUMMARY OF THE INVENTION

The invention in its most general terms comprises an artificial hip socket in which a socket-like bearing insert for receiving the ball is insertable. A groove is provided near the inner edge of the socket. An annular bearing preferably a split ring, is also provided having a front circumferential notch. A retaining ring is used to firmly hold the ball of the femur in the socket and bearings, in conjunction with the groove and notch.

The artificial femur has a ball typically 22 mm or 32 mm in diameter made of resistant metal such as Vitallium or stainless steel. A stem is provided for the ball so that the femur can receive the ball in the right position after the diseased head has been removed. The socket itself is also preferably made of a similar metal such as Vitallium, but the bearing material is preferably made of a low friction plastic (e.g. high molecular weight polyethylene) having a slight flexibility. The retaining ring is preferably made of a resistant metal such as Vitallium or stainless steel.

The bearings sit adjacent to one another within the socket after the femoral head has already been inserted into the bearing insert. In practice the annular bearing is passed over the head and sits on the neck of the femur ball so that after the ball has been inserted into the bearing insert within the socket it is then moved over the ball to fit against the bearing insert and the entire assembly is locked by means of the retaining ring which fits into the groove on the inner surface or edge of the socket and on the notch.

The invention provides versatility at the time of first use, offering a choice between a polycentric type of prosthesis or a total hip device. The parts may be interchangeable at a later date in a second surgical procedure so that a polycentric type may be converted to a total type by changing only the socket. In using the invention the various components may be inserted assembled with no requirement for exact angulation of the socket components. They may also be inserted separately and assembled after the desired angle has been made for the socket. The artificial hip joint of this invention may be readily assembled or disassembled with great ease and with no special tools and tolerates greater error than in prior art devices. Further, various individual parts which may be loosened or worn may be changed without the necessity of replacing the entire hip joint.

By use of this invention, a great deal of surgical procedure and operating time is avoided when or if it becomes necessary to repair or replace any component of the artificial joint after it has first been implanted onto the biological surface.

BRIEF DESCRIPTION OF DRAWINGS

FIG. 1 is an exploded view of one embodiment of this invention where the socket is of a cementable type.

FIG. 2 is a perspective view of a socket of the bicentric type.

FIG. 3 is a perspective view enlarged of the split ring bearing.

FIG. 4 is a front view of the split ring bearing of FIG. 3.

FIG. 5 is a perspective view of two separate hemispheres forming the split ring bearing.

FIG. 6 is a front view of FIG. 5.

FIG. 7 is a cross-sectional view of the components of the invention in assembly.

SPECIFIC EXAMPLES OF INVENTION

Referring now to the drawings there is illustrated therein an artificial hip socket 10 having a cavity 13 of generally hemispheric and cylindrical shape with a circumferential inner groove 11 and outer grooves 12 which are useful for cementing where desired to tissue of the body. Fitting within the cavity 13 is a bearing insert 50. Insert 50 has a cavity 51 for supporting the ball 40, mounted on the neck 42 of artificial femur 41. An annular bearing 60 is provided which has a transverse split 61 enabling it to be forced over onto the neck 42 of the artificial femur 41. The bearing 60 has a circumferential notch 60a in front so that there is a front protuberance 60b. When the parts are assembled, clasp-like locking ring 30 keeps all the parts firmly in position by fitting into groove 11 on the inner circumference of the socket 10, and notch 60a in insert 60. The holes 30a permit easy manipulation of the ring by forceps or long-nose pliers for assembly or disassembly.

In place of the cementable socket 12 a bicentric socket 15 can be used which has a similar cavity 18 and circumferential groove 16 but has a smooth outer surface 17 rather than grooves on the surface.

Similarly in place of the split ring bearing 60 a bearing 160 comprising a pair of semi-circular members 160a and 160b can be put around the neck 42 of the artificial femur and will function in a similar manner. These likewise have an outer groove 160c.

I claim:

1. An artificial hip joint comprising an artificial hip socket having a first cavity and an opening in a surface of the socket communicating with the first cavity, an annular groove formed in the first cavity adjacent said opening, a sectionalized bearing insert registerably positioned in the first cavity inwardly of said groove, said bearing insert having a second cavity of spherical configuration greater in scope than hemispherical, a femoral component having a ball extending from a neck of reduced diameter, said neck extending through said socket opening positioning said ball in operative, retained engagement in said second cavity, said bearing insert having inner and outer sections, each section being formed with a complementary component of said second cavity, the cavity component of said inner section being approximately hemispherical, said outer section being annular in shape and having an outer surface portion opposite the cavity component thereof adapted to align with said annular groove when said outer section is in operative position in said first cavity, and an open annular spring locking ring having opposite ends formed with tool engaging openings, said locking ring being removably engaged in said annular groove in abutment with said outer surface portion of the bearing insert outer section, said locking ring, when in said groove engagement, being visibly exposed and removably retaining said annular outer section in said first cavity in operative engagement with the inner section whereby said ball is retained in said second cavity, said annular outer section being formed to expand over said ball when the latter is removed from said first cavity.

2. The artificial hip joint defined in claim 1 in which the outer surface portion of said annular outer section of the bearing insert is formed as a circumferential notch.

3. The artificial hip joint defined in claim 1 in which said annular outer section of the bearing insert is formed as a split ring for said expansion over the ball.

4. The artificial hip joint defined in claim 1 in which said annular outer section of the bearing insert is formed as two separate semi-circular members for said expansion over the ball.

5. The artificial hip joint defined in claim 1 in which said hip socket has a smooth outer surface to engage a patient's acetabulum in serving as a polycentric prosthesis.

6. The artificial hip joint defined in claim 5 in which said removability of said annular outer section permits replacement of said smooth outer surfaced hip socket by a hip socket having exterior grooves and cemented into a deteriorated acetabulum to convert, by reassembly, to a total hip prosthesis without replacing said femoral component.

* * * * *

REEXAMINATION CERTIFICATE (2092nd)

United States Patent [19]

Ramos

[11] B1 4,380,090

[45] Certificate Issued Sep. 21, 1993

[54] HIP PROSTHESIS

[76] Inventor: Pedro A. Ramos, 1960 SW. 27th Ave., Miami, Fla.

Reexamination Request:
No. 90/002,753, Jun. 5, 1992

Reexamination Certificate for:
| | |
|---|---|
| Patent No.: | 4,380,090 |
| Issued: | Apr. 19, 1983 |
| Appl. No.: | 356,881 |
| Filed: | Mar. 10, 1982 |

Related U.S. Application Data

[63] Continuation-in-part of Ser. No. 286,532, Jul. 24, 1981, abandoned, which is a continuation-in-part of Ser. No. 177,791, Aug. 13, 1980, abandoned.

[51] Int. Cl.$^5$ .............................................. A61F 2/34
[52] U.S. Cl. ........................................................ 623/22
[58] Field of Search ........................ 623/16, 18, 22, 23

[56] References Cited

U.S. PATENT DOCUMENTS

| | | |
|---|---|---|
| Re. 28,895 | 7/1976 | Noiles . |
| 1,891,804 | 12/1932 | Flumerfelt . |
| 1,894,309 | 1/1933 | Flumerfelt . |
| 1,985,728 | 12/1934 | Ingersoll . |
| 2,301,810 | 11/1942 | Phillips . |
| 3,067,740 | 12/1962 | Haboush . |
| 3,220,755 | 11/1965 | Gottschald et al. . |
| 3,401,965 | 9/1968 | Wehner . |
| 3,717,932 | 2/1973 | Brainin . |
| 3,797,128 | 3/1974 | Amano . |
| 3,806,960 | 4/1974 | Weber . |
| 3,813,699 | 6/1974 | Giliberty . |
| 3,818,512 | 6/1974 | Shersher ............... 623/22 |
| 3,840,904 | 10/1974 | Tronzo . |
| 3,848,272 | 11/1974 | Noiles ................... 623/22 |
| 3,863,273 | 2/1975 | Averill .................. 623/23 |
| 3,864,758 | 2/1975 | Yakich . |
| 3,875,593 | 4/1975 | Shersher ............... 623/22 |
| 3,903,549 | 9/1975 | Deyerle . |
| 3,916,451 | 11/1975 | Buechel et al. ........ 623/19 |
| 3,978,528 | 9/1976 | Crep ..................... 623/19 |
| 4,004,300 | 1/1977 | English ................. 623/23 |
| 4,051,559 | 10/1977 | Pifferi . |
| 4,077,070 | 3/1978 | Siwash . |
| 4,159,544 | 7/1979 | Termanini .............. 623/22 |
| 4,206,517 | 6/1980 | Pappas et al. . |
| 4,230,415 | 10/1980 | Scheerer . |
| 4,241,463 | 12/1980 | Khovaylo .............. 623/23 |
| 4,365,358 | 12/1982 | Judet, deceased et al. .......... 623/22 |

FOREIGN PATENT DOCUMENTS

| | | |
|---|---|---|
| 2039731 | 2/1971 | Fed. Rep. of Germany . |
| 1943598 | 3/1971 | Fed. Rep. of Germany . |
| 2301810 | 1/1972 | Fed. Rep. of Germany . |
| 2323456 | 11/1974 | Fed. Rep. of Germany . |
| 2628530 | 12/1976 | Fed. Rep. of Germany . |
| 2714387 | 11/1977 | Fed. Rep. of Germany . |
| 2826690 | 2/1979 | Fed. Rep. of Germany . |
| 2903366 | 8/1979 | Fed. Rep. of Germany . |
| 2437199 | 9/1978 | France . |
| 1325534 | 8/1973 | United Kingdom . |
| 1362187 | 7/1974 | United Kingdom . |
| 1415736 | 11/1975 | United Kingdom . |
| 1531487 | 11/1978 | United Kingdom . |

OTHER PUBLICATIONS

Waldes Truacrc ® Title Page and copyright information of Technical Manual Waldes Kohinoor, Inc., ©1958, 1959, 1960, 1961, 1962, 1963, 1964, 1966.
Deposition Transcript of Pedro A. Ramos, Sep. 7, 1990.
Deposition Transcript of Lee A. Swanger, Mar. 13, 1992.
"Bateman UPF Universal Proximal Femur", 3M, St. Paul, Minn., 11 pages (1980).
"Giliberty II Bipolar Endoprosthesis", Brochure No. B-1160, Zimmer, Warsaw, Ind., 8 pages (1980).
"UHI Universal Head System", Osteonics Corp., 4 pages (1980).

*Primary Examiner*—David J. Isabella

[57] ABSTRACT

An artificial hip joint including an artificial hip socket having a first cavity and an inner groove, a bearing insert registerable with said first cavity and itself having a second cavity and an annular bearing which has a circumferential front notch. The bearings abut the inner walls of said first cavity to define a central cavity. A locking ring is registerable with said notch and groove. An artificial femur component has a ball registerable and lockable in said central cavity.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 2, 3, 4 and 5 is confirmed.

Claim 6 is determined to be patentable as amended.

6. The artificial hip joint defined in claim [5] *1* in which said [removability of said annular outer section permits replacement of said smooth outer surfaced hip socket by a] hip socket [having] *has* exterior grooves [and] *for securing said socket when* cemented into a deteriorated acetabulum [to convert, by reassembly, to a total hip prosthesis without replacing said femoral component].

* * * * *